United States Patent [19]

Yoshikuni et al.

[11] Patent Number: 5,292,750
[45] Date of Patent: Mar. 8, 1994

[54] THERAPEUTIC AGENTS

[75] Inventors: Yoshiaki Yoshikuni, Uji; Nobutoshi Ojima, Moriyama; Kazuya Mori, Kyoto, all of Japan

[73] Assignee: Nippon Shinyaku Co. Ltd., Japan

[21] Appl. No.: 941,792

[22] Filed: Sep. 8, 1992

Related U.S. Application Data

[60] Division of Ser. No. 747,454, Aug. 12, 1991, Pat. No. 5,192,772, which is a continuation of Ser. No. 281,495, Dec. 8, 1988, abandoned.

[30] Foreign Application Priority Data

Dec. 9, 1987 [JP] Japan .................................. 62-311348

[51] Int. Cl.$^5$ ............................................. A61K 31/445
[52] U.S. Cl. ................................... 514/315; 514/317; 514/318; 514/319; 514/321; 514/328
[58] Field of Search ..................... 514/230.5, 315, 321, 514/317, 319, 318, 326, 328

[56] References Cited

U.S. PATENT DOCUMENTS

| | | | |
|---|---|---|---|
| 4,182,767 | 1/1980 | Murai et al. | 514/315 |
| 4,260,622 | 4/1981 | Junge et al. | 514/315 |
| 4,312,872 | 1/1982 | Junge et al. | 514/315 |
| 4,348,402 | 9/1982 | Kinast et al. | 514/315 |
| 4,533,668 | 8/1985 | Matsumura et al. | 514/321 |
| 4,639,436 | 1/1987 | Junge et al. | 514/230.5 |

FOREIGN PATENT DOCUMENTS

| | | |
|---|---|---|
| 0034784 | 7/1981 | European Pat. Off. . |
| 202661 | 1/1986 | European Pat. Off. . |
| 295538 | 6/1988 | European Pat. Off. . |
| 2067989 | 9/1981 | United Kingdom . |
| 8703903 | 3/1987 | World Int. Prop. O. . |

OTHER PUBLICATIONS

Dictionary of Organic Compounds, 5th Edition, 2nd Supplement, Chapman & Hall, publication 1984.
Blomback et al., Plasma Proteins, 1976, pp. 288–308.
Aoki and Harpel, Seminars in Thrombosis and Hemostasis-vol. 10, No. 1, 1984.

*Primary Examiner*—Frederick E. Waddell
*Assistant Examiner*—K. Weddington
*Attorney, Agent, or Firm*—Rosenman & Colin

[57] ABSTRACT

Compounds are described which are useful for lowering the activity of $\alpha_2$-PI, for the treatment of myocardial infarctions and cerebral infarctions, as urokinase secretion accelerators, as antithrombotic agents and to accelerate the fibrinolysis accelerating effect.

2 Claims, No Drawings

THERAPEUTIC AGENTS

CROSS-REFERENCE

This is a division of Ser. No. 747,454 filed Aug. 12, 1991; now U.S. Pat. No. 5,192,772, which is a continuation of Ser. No. 281,495, filed Dec. 8, 1988, abandoned.

The present invention relates to compounds useful as $\alpha_2$-plasmin inhibitor depressants, urokinase secretion accelerators, antithrombotic agents, accelerators for accelerating the fibrinolysis accelerating effect and for the treatment of myocardial and cerebral infarctions in humans and animals.

It is known in the art that for the formation of hemostatic thromboses caused by physical damage to the blood vessels, aggregation of platelets and subsequent precipitation of fibrin are inevitably required. On the other hand, thromboses inhibit blood flow in the blood vessels thus causing ischemia or necrosis of tissue resulting in myocardial infarctions or cerebral infarctions. Thus, the living body is prepared with a mechanism for removing excess thromboses in the blood vessels where fibrinolysis by the plasminogen-plasmin system plays a major role in the mechanism.

It is also known in the art that plasminogen is activated with a plasminogen activator for conversion into plasmin and that plasmin decomposes fibrin (fibrinolysis). An abnormality in this mechanism would cause diseases such as myocardial or cerebral infarctions.

One method of treating such conditions involve fibrinolytic therapy in which the formed thrombus is lysed to improve the ischemic state of the tissue. This is achieved by administering plasminogen activators such as urokinase, streptokinase and the like. Thus, a substance which accelerates the secretion ot urokinase would be a useful drug in the therapy of thromboses.

The living body is also prepared with a mechanism for protecting against excessive fibrinoloysis. It is known, for example, that $\alpha_2$-plasmin inhibitors (hereinafter referred to as "$\alpha_2$-PI") which is a plasmin inhibitor instantaneously inhibits plasmin activity thus inhibiting fibrinoloysis. Therefore, $\alpha_2$-PI acts as a treatment inhibitor in the therapy of fibrinoloysis and is also formed as a type of protein in the acute phase to become one of the causes of postoperative thromboses.

Thus, a drug which lowers the activity of an $\alpha_2$-PI would enhance the effect in therapy of fibrinolysis and would prevent postoperative thromboses from forming.

Thus, one of the objects of the present invention is to provide an $\alpha_2$-PI inhibitor for administration for the treatment of myocardial infarctions or cerebral infarctions.

A further object of the present invention is to provide a substance for accelerating the secretion of urokinase since urokinase is a plasminogen activator.

It has now been discovered that a compound selected from the group consisting of:
a. a compound of the formula

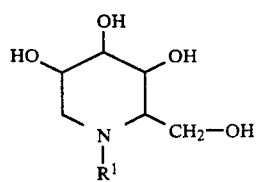

(I)

,a pharmaceutically acceptable acid addition salt thereof or a quaternary salt thereof wherein $R^1$ is hydrogen, alkyl of 1 to 10 carbon atoms, carboxyalkyl of 1 to 10 carbon atoms in the alkyl moiety, lower alkyloxycarbonylalkyl of 1 to 10 carbon atoms in the alkyl moiety, hydroxyalkyl of 1 to 10 carbon atoms in the alkyl moiety, cycloalkyl lower alkyl wherein the cycloalkyl moiety is of 3 to 7 carbon atoms, aryl lower alkyl, aryloxy lower alkyl, alkenyl of 2 to 10 carbon atoms or arylalkenyl of 2 to 10 carbon atoms in the alkenyl moiety;

b. nojirimycin or a pharmaceutically acceptable acid addition salt thereof;

c. 1,4-bis(3-moranolino-1-propenyl)benzene or a pharmaceutically acceptable acid addition salt thereof; and d. castanospermine, are useful for lowering the activity of $\alpha_{21}$-PI. Those compounds are also useful, therefore, in the treatment of myocardial and cerebral infarctions and for the treatment of thrombosis in humans and animals.

A compound selected from the group consisting of:
a. a compound of the formula

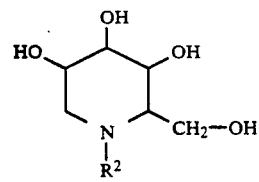

(II)

or a pharmaceutically acceptable acid addition salt thereof or a quaternary salt thereof wherein $R^2$ is hydrogen, alkyl of 1 to 10 carbon atoms, carboxyalkyl of 1 to 10 carbon atoms in the alkyl moiety, lower alkyloxycarbonylalkyl of 1 to 10 carbon atoms in the alkyl moiety, hydroxyalkyl of 1 to 10 carbon atoms, cycloalkyl lower alkyl of 3 to 7 carbon atoms in the cycloalkyl moiety, arylalkyl of 1 to 10 carbon atoms in the alkyl moiety, aryloxyalkyl of 1 to 10 carbon atoms in the alkyl moiety, alkenyl of 2 to 10 carbon atoms, hydroxyalkenyl of 2 to 10 carbon atoms, arylalkenyl of 2 to 10 carbon atoms in the alkenyl moiety, aryloxyalkenyl of 2 to 10 carbon atoms in the alkenyl moiety or lower alkylcarbamoylalkyl of 1 to 10 carbon atoms in the alkyl moiety;

b. nojirimycin or a pharmaceutically acceptable acid addition salt thereof;

c. 1,4-bis(3-moranolino-1-propenyl)benzene or a pharmaceutically acceptable acid addition salt thereof; and d. castanospermine, are useful as urokinase secretion accelerators and for accelerating the fibrinoloysis accelerating effect.

The term alkyl as used herein refers to an alkyl moiety having 1 to 10 carbon atoms, preferably, lower alkyl. Representative lower alkyl moieties are those containing from 1 to 6 carbon atoms such as methyl, ethyl, propyl, butyl and the like.

Carboxyalkyl groups include those containing from 1 to 10 carbon atoms in the alkyl moiety, but those having a lower alkyl moiety are preferred. Representative carboxyalkyl moieties include carboxymethyl, carboxyethyl and carboxypropyl.

Alkyloxycarbonylalkyl includes those moieties having 1 to 10 carbon atoms in each of the alkyl moieties. It is preferred, however, that each of the alkyl moieties be a lower alkyl moiety. Representative moieties include methoxycarbonylmethyl, methoxycarbonylethyl, methooxycarbonylpropyl, methoxycarbonylbutyl, ethoxycarbonylmethyl, ethoxycarbonylethyl, ethoxycarbonylpropyl and ethoxycarbonylbutyl.

The hydroxyalkyl moiety contains from 1 to 10 carbon atoms in the alkyl moiety. Preferred hydroxyalkyl groups are hydroxy lower alkyl moieties. Representative hydroxy lower alkyl moieties include hydroxymethyl, hydroxyethyl, hydroxypropyl and hydroxybutyl.

Cycloalkyl alkyl moieties, preferably contain 3 to 7 carbon atoms in the cycloalkyl moiety and 1 to 10 carbon atoms in the alkyl moiety. Preferred groups include cycloalkyl alkyl moieties of 3 to 5 carbon atoms in the cycloalkyl moiety and wherein the alkyl moiety is a lower alkyl group. Representative moieties include cyclopropylmethyl, cyclobutylmethyl and cyclopentylmethyl.

Arylalkyl moieties contain from 1 to 10 carbon atoms in the alkyl moiety, but preferably have lower alkyl moieties. The aryl moiety is preferrably phenyl or naphthyl. Representative arylalkyl moieties include benzyl, phenethyl, phenylpropyl, phenylbutyl, phenylpentyl, naphthylmethyl, naphthylethyl, naphthylpropyl and naphthylbutyl.

Aryloxyalkyl moieties are those of 1 to 10 carbon atoms in the alkyl moiety, but preferably those wherein the aryl moeity is phenyl or naphthyl and the alkyl moiety is a lower alkyl moiety. Representative groups include phenoxymethyl, phenoxyethyl, phenoxypropyl, phenoxybutyl, naphthyloxymethyl, naphthyloxyethyl, naphthyloxypropyl and naphthyloxybutyl.

The alkenyl moieties contain from 2 to 10 carbon atoms; it is preferred that they be lower alkenyl moieties. Representative alkenyl moieties include vinyl, propenyl and butenyl.

Hydroxyalkenyl are those moieties of 2 to 10 carbon atoms in the alkenyl moiety. Preferred hydroxyalkenyl moieties are hydroxy lower alkenyl moieties. Representative groups include hydroxyvinyl, hydroxypropenyl and hydroxybutenyl.

Arylalkenyl groups are those containing from 2 to 10 carbon atoms in the alkenyl group, but preferably are those wherein the aryl moiety is phenyl or naphthyl and the alkenyl moiety is a lower alkenyl moiety. Representative groups include phenylvinyl, phenylpropenyl, phenylbutenyl, naphthylvinyl, naphthylpropenyl and naphthylbutenyl.

Aryloxyalkenyl moieties contain from 2 to 10 carbon atoms in the alkenyl moiety, but preferably are those wherein the aryl moiety is phenyl or naphthyl and the alkenyl moiety is a lower alkenyl moiety.

Alkylcarbamoylalkyl moieties are those containing from 1 to 10 carbon atoms in each of the alkyl moieties, but preferably are those wherein each of the alkyl moieties is a lower alkyl group.

The arylalkyl, aryloxyalkyl and arylalkenyl moieties may optionally be substituted.

In addition to the compounds described above, the present invention also includes nojirimycin which has an OH group at 1-position of the basic structure of moranoline and derivatives thereof, for example, N-substituted derivatives. These compounds exhibit similar activities to the moranoline derivatives, i.e., the unsubstituted derivatives, and are included within the present invention.

Compounds having the moranoline basic structure as bis-form are also included in the present invention. These compounds exhibit the therapeutic utilities described above.

Representative examples of those compounds include nojirimicin and pharmaceutically acceptable salts thereof such as 1,4-bis-(3-moranolino-1-propenyl)benzene and pharmaceutically acceptable salts thereof. These compounds also exhibit an excellent $\alpha_2$-PI lowering activity and urokinase secretion accelerating activity.

The compounds of the present invention can be prepared by conventional procedures per se known. The following nonlimitative examples represent typical procedures for preparing N-butylmoranoline.

PREPARATION EXAMPLE 1

Moranoline, 50 g, 126 g of n-butyl bromide and 170 g of potassium carbonate were added to 1300 ml of dimethylformamide. The mixture was stirred at room temperature for 7 days to complete the reaction. After impurities were removed by filtration, the solvent was distilled off under reduced pressure and 1000 ml of a strongly acidic ion exchange resin Dowex 50 W×2 (H+) was passed. After thoroughly washing with water, elution was performed with 1N ammonia water. The eluate was concentrated under reduced pressure. Thereafter, 50 ml of methanol was added to the concentrate. The mixture was allowed to stand at room temperature and the formed crystals (47 g) were collected.

After the crystals were dissolved in 500 ml of methanol with heating, the solution was cooled to room temperature and then treated with activated charcoal. After concentrating to about 100 ml, the concentrate was allowed to stand at room temperature and 40 g of crystals precipitated were collected. After the crystals were dissolved in 200 ml of methanol with heating, the solution was gently concentrated. The concentrate was allowed to stand at room temperature and crystals precipitated were collected. The crystals were thoroughly dried at 70° C. under reduced pressure to give 34 g of objective N-(n-butyl)moranoline.

Yield, 50.6%; melting point, 128°–129° C.
Elemental analysis:
Calcd. (%): C: 54.78 H: 9.65 N: 6.39.
Found (%) : C: 54.57 H: 9.65 N: 6.60.
$[\alpha]D^{24} = -14.59$ (1%, water)
$^1$H-NMR: 0.88 (3H, t, J=7.2 Hz, CH$_3$CH$_2$CH$_2$CH$_2$—),1.16–1.56 (4H, m, CH$_3$CH$_2$CH$_2$CH$_2$—), 2.17–2.36 (2H, m, (CH$_3$CH$_2$CH$_2$CH$_2$—), 2.48–2.82 (2H, m, H-1a, H-5), 3.02 (1H, dd, J=5.1, 11.4 Hz, H-1e), 3.22 (1H, t, J=9.0 OHz, H-1e), 3.66 (1H, t, J=9.4 Hz, H-3), 3.44–3.6 (1H, m, H-2), 3.74–3.96 (H×2, dd×2, H$_6$, H$_6$)

PREPARATION EXAMPLE 2

Moranoline, 5 g, 13 g of n-butyl bromide and 17 g of potassium carbonate were added to 130 ml of dimethylformamide. The mixture was reacted at 100° C. for 5 hours. Then, the reaction mixture was treated in a manner similar to Preparation Example 1 to give 5.1 g of N-(n-butyl)moranoline. Yield, 75.8%.

PREPARATION EXAMPLE 3

To 100 ml of methanol was added 5 g of moranoline. While stirring at room temperature, a solution of 20 ml of n-butylaldehyde in 50 ml of methanol having dissolved therein 0.7 g of hydrogen chloride and 3 g of NaCNCH₃ were added to the mixture. The reaction was carried out overnight. After completion of the reaction, the solvent was removed under reduced pressure. The residue was dissolved in followed by partition with chloroform. The aqueous phase was passed through a column of 200 ml Diaion SA-11A (OH⁻) type followed by thorough washing with water. The passing liquid was combined with the washing liquid. The mixture was passed through a column of 200 ml Dowex 50 W×28 (H⁺) type. After thoroughly washing, elution was conducted with 1N ammonia water. After the solvent was distilled off under reduced pressure, the eluate was crystallized from ethanol. Recrystallization from ethanol gave 5.1 g of N-(n-butyl)-moranoline. Yield, 75.8%.

Typical examples of the compounds in accordance with the present invention include the following compounds.
Compound No. 1: Moranoline
Compound No. 2: N-methylmoranoline
Compound No. 2a: N-(n-Butyl)moranoline
Compound No. 3: N-5-Methoxycarbonylpentylmoranoline tosylate
Compound No. 4: N-Hydroxyethylmoranoline
Compound No. 5: (N-Methoxycarbonylbutyl)moranoline
Compound No. 6: Nojirimycin bisulfite
Compound No 7: 1,4-Bis-(3-moranolino-1-propenyl)-benzene dihydrochloride
Compound No. 8: N-Hexylmoranoline tosylate
Compound No. 9: N-Isoprenylmoranoline
Compound No. 10: N-(2-Hydroxydecyl)moranolinetosylate
Compound No. 11: N-10-Carboxydecylmoranoline sodium salt
Compound No. 12: N-(3-Phenylpropyl)moranolinetosylate
Compound No. 13: N-Benzylmoranoline tosylate
Compound No. 14: N-Cinnamylmoranoline hydrochloride
Compound No. 15: N-4-Phenylbutylmoranoline tosylate
Compound No. 16: N-(2-Phenoxyethyl)moranoline
Compound No. 17: N-(3-Phenoxypropyl)moranoline tosylate
Compound No. 18: N-5-(Phenylpentyl)moranolinetosylate
Compound No. 19: N-(2-Cyclopentylethyl)moranoline tosylate
Compound No. 20: N-[3-(3-Methoxyethoxyphenyl)-2-butenyl]moranoline
Compound No. 21: N,N-Dimethylmoranoline ammonium iodide
Compound No. 22: N-Ethylmoranoline
Compound No. 23: N-Cinnamylmoranoline
Compound No. 24: N-Geranylmoranoline tosylate
Compound No. 25: N-(2-Hydroxy-3-phenoxypropyl)-moranoline tosylate
Compound No. 26: N-Farnesylmoranoline tosylate
Compound No. 27: N-10-(N-Methylcarbamoyl)decylmoranoline
Compound No. 28: N-(4-Phenyl-3-butenyl)moranoline tosylate
Compound No. 29: N-(3-Phenyl-2-methyl-2-propenyl)-moranoline
Compound No. 30: N-(3-γ-Chlorophenoxypropyl)-moranoline
Compound No. 31: N-γ-Methyl-4-bromocinnamyl)-moranoline
Compound No. 32: N-[4-(3-Fluoro-4-methylphenyl)-butyl]-moranoline
Compound No. 33: N-(p-Ethoxycinnamyl)moranoline
Compound No. 34: N-(p-Isopropoxycinnamyl)moranoline
Compound No. 35: N-γ-Methyl-m-methylcinnamyl)-moranoline
Compound No. 36: N-(4-m-Methoxyphenyl-3-pentenyl)-moranoline
Compound No. 37: N-(p-Ethoxycarbonylphenoxyethyl)-moranoline[emiglitate]
Compound No. 38: Castanospermine In addition to those described above, the compounds in accordance with the present invention further include the following compounds.
N-Isobutylmoranoline tosylate
N-Hydroxyethylmoranoline tosylate
N-Aminomoranoline hydrobromide
N-Methoxyethylmoranoline tosylate
N-Methoxyethoxyethylmoranoline tosylate
N-Decylmoranoline tosylate
N-(2-Hydroxyhexadecyl)moranoline tosylate
N-(2-Hydroxy-3-p-tolyloxypropyl)moranoline tosylate
N-(2-Hydroxy-3-p-methoxyphenyloxypropyl)moranoline tosylate
N-(2-Hydroxy-3-p-chlorophenyloxypropyl)moranoline tosylate
N-3-Carbamoylpropylmoranoline
N-Nonylmoranoline tosylate
N-Undecylmoranoline tosylate
N-(2-Hydroxytetradecyl)moranoline tosylate
N-(4,4-Diphenyl-3-butenyl)moranoline
N-5-Carboxypentylmoranoline
N-farnesylmoranoline
N-(γ-Methyl-4-chlorocinnamyl)moranoline
N-(γ-Methyl-4-methylcinnamyl)moranoline
N-(4-p-Chlorophenyl-3-pentenyl)moranoline
N-(4-m-Chlorophenyl-3-pentenyl)moranoline
N-(4-o-Chlorophenyl-3-pentenyl)moranoline
N-(4-p-Phenoxyphenyl-3-pentenyl)moranoline
N-(4-p-Ethoxyphenyl-3-pentenyl)moranoline
N-(m-Methoxycinnamyl)moranoline
N-[3-(3-Chlorophenyl)-2-butenyl]moranoline
N-[4-(4-Chlorophenyl)-3-butenyl]moranoline
N-(4-Carboxylcinnamyl)moranoline hydrochloride
N-(3-Carboxy-2-propenyl)moranoline
N-(m-Triethylammonioethoxycinnamyl)moranoline dipicrate
N-Isopropylmoranoline
N-(p-Trimethylammonioethyoxycinnamyl)moranoline-chloride hydrochloride When the compounds of the present invention are administered as pharmaceuticals, to humans and animals, they are given per se or as a pharmaceutical composition containing, for example, 0.1 to 99.5% (more preferably, 0.5 to 90%) of active ingredient in combination with a pharmaceutically acceptable carrier.

The compounds of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

As to carriers, one or more liquid, solid or semisolid diluent, filler and other auxillary agents for pharmaceutical preparations may be used. It is desired that the pharmaceutical compositions are administered in unit dosage form.

Oral administration can be effected utilizing solid and liquid dosage unit forms such as powders, tablets, capsules, granules and the like.

Powders are prepared by comminuting the compound to a suitable fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder as carboxymethyl cellulose, an alginage, gelatin, or polyvinyl pyrrolidone, a solution retardant such as paraffin, a resorption accelerator such as a quarternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically acctable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations or oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example flavored aqueous solution, while elixirs are prepared through myristyl palmitate or mixtures thereof.

In determining the specific dosage for each treatment, a number of factors such as the age of the patient, body weight, severity of condition, administration route, and the like must be considered. Generally, from about 50 mg to 3000 mg per day of a compound of the present invention should be administered to a human adult preferably from 500 mg to 1000 mg per day.

It is preferred that the administration be divided so that administration takes place 2 or 3 times per day.

The following nonlimitative examples more particularly illustrate the present invention.

The $\alpha_2$-PI lowering activity and the urokinase secretion accelerating activity, as well as, the low toxicity of the compounds of the present invention are illustrated by the data set forth below.

Activity in vitro

It is known that human hepatic cancer-derived HepG2 cells synthesize and secrete $\alpha_2$-plasmin inhibitor ($\alpha_2$-PI). The HepG2 cells, $2 \times 10^6$, were inoculated on a plastic culture plate (diameter of 100 mm) made by Falcon Inc. and cultured in Eagle's minimum medium containing 10% bovine fetal serum.

Three days after, cells adhered to the bottom of the plate were washed twice with Dulbecco's phosphate buffer followed by culturing in 8 ml of serum-free Eagle's medium (containing no Phenol Red) containing 200 $\mu$g/ml of a specimen of the compound of the present invention for further 3 to 4 days. After culture, 7 ml of the medium was collected and concentrated to about 1 ml using Centriflow (CF25) made by Falcon Inc. The concentrate was further freeze dried.

To the freeze dried sample, 0.7 ml of 50 mM Tris buffer containing 8.1 mg/ml of monomethylamine hydrochloride was added to dissolve therein, whereby the solution was concentrated to 10-fold.

To 100 $\mu$l of the concentrated sample, 50 $\mu$l of 15 mCU plasmin solution was added and further 50 $\mu$l of 0.25 $\mu$mole S-2251 synthetic chromogenic substrate solution was added thereto followed by reacting at 37° C. for 10 minutes. By adding 1 ml of 2% citrate solution, the reaction was stopped. p-Nitroanilide released from the S-2251 substrate was measured at O.D. of 403 nm.

A sample in which decomposition of the S-2251 substrate was measured using the aforesaid Tris buffer instead of the concentrated sample was made a control showing 100% plasmin activity and the concentrated sample cultured without adding a test compound was made a control showing 100% $\alpha_2$-PI acitivity. The results were calculated according to the following equation.

$$\alpha_2\text{-}PI \text{ Activity } (\%) = \frac{A_1 - A_2}{A_1 - A_3} \times 100$$

wherein $A_1$, $A_2$, and $A_3$ represent absorbance in 100% control, absorbance when the concentrated sample was used and absorbance in a $\alpha_2$-PI activity 100% control, respectively. The number of the samples was 3, respectively. The results are shown in Table 1. It is evidence that the compounds of the present invention can lower the $\alpha_2$-PI acitivity.

TABLE 1

| Sample Compound No. | $\alpha_2$-PI Activity (%) | Sample Compound No. | $\alpha_2$-PI Activity (%) |
|---|---|---|---|
| Control | 100 | 11 | 88 |
| 1 | 63 | 12 | 50 |
| 2 | 62 | 13 | 80 |
| 2a | 59 | | |
| 3 | 70 | 14 | 51 |
| 4 | 70 | 15 | 39 |
| 5 | 79 | 16 | 74 |
| 6 | 67 | 17 | 65 |
| 7 | 85 | 18 | 20 |
| 8 | 56 | 19 | 63 |
| 9 | 55 | 20 | 37 |

Activity in vivo

Three (3) male Beagle dogs were used for the control group and the administered group, respectively, as animals to be administered.

A test sample (Compound No. 2) was dissolved in a concentration of 10 mg 0.1 ml, using 0.1M phosphage buffer (pH 7.2). After dissolution, the solution was sterilized by filtration through a sterile filter (pore size, 0.2 $\mu$m) and then 0.3 ml of the solution was administered per 1 kg of body weight (30 mg/kg). The administration was made through the right front limb vein for consecutive 7 days. Collected blood was mixed with 3.8% sodium citrate in a ratio of 1:9 by volume. By centrifugation at 3000 rpm for 15 minutes, plasma was isolated.

The $\alpha_2$-PI activity was measured as an inhibition activity against decomposition of plasmin with the synthetic chromogenic substrate S-2251. The results of measurement are shown as change in inhibition activity after administration based on 100% of the plasmin inhibition activity prior to administration of the test sample (Table 2). The sample number in each group was 3 samples.

The $\alpha_2$-PI activity was obviously depressed by consecutive administration of the test compound in a dose of 30 mg/kg.

TABLE 2

| Day | [$\alpha_2$-PI activity (%)] | | | | | | | |
|---|---|---|---|---|---|---|---|---|
| | 0 | 1 | 2 | 3 | 4 | 5 | 6 | 7 |
| C | 100 | 98 | 92 | 94 | 96 | 98 | 100 | 106 |
| Sample | 100 | 95 | 83 | 84 | 76 | 75 | 86 | 89 |

C: control
Sample: test sample

Test on fibrinolysis in vitro

A test sample (Compound No. 2) was consecutively administered to Beagle dogs in a dose of 30 mg/kg once a day. Plasma was isolated prior to and 4 days after the administration. The $\alpha_2$-PI activity in plasma was measured and at the same time, fibrin clot was formed in vitro using the plasma. When urokinase as a thrombolytic agent was acted on the fibrin clot, a degree of lysis was compared between plasma prior to the administration and plasma 4 days after the adminsitration.

To 500 $\mu$l of the isolated plasma, 40 $\mu$l of $^{125}$I-fibrinogen (0.1 mCi/ml) was added and 50 $\mu$l each of the mixture was dispensed in a test tube. 5 $\mu$l each of a solution mixture of 25 U/ml thrombin and 0.5M calcium chloride was added to each test tube, which was incubated at 37° C. for 30 minutes to prepare fibrin clots. Solutions of 15 and 30 U/ml of urokinase in 2% albumin solution and the resulting solution were charged in each test tube by 1 ml each.

After incubating at 37° C. for 12 hours, 25 $\mu$l of the supernatant was collected in an RAI tube and $^{125}$I-fibrin decomposition products isolated in the supernatant were measured with a y-counter. The sample number was 3 in each group.

As shown in Table 3, it is clear that when the plasma having lowered $\mu_2$-PI activity was used, lysis of the fibrin clots was accelerated by administration of the test compound, as compared to the plasma prior to the administration.

TABLE 3

| | Rate of Lysis of Fibrin Clot (%) | |
|---|---|---|
| Urokinase Activity | Prior to Administration | 4 Days After Administration |
| 0 U | 18.1 | 21.5 |
| 15 U | 37.4 | 63.8 |
| 30 U | 70.0 | 93.7 |

Thrombolytic test in vitro

Thrombolytic activity-inducing ability in the established vascular endothelial cell culture system was examined using CPAE (calf pulmonary artery endothelia).

CPAE cells were purchased from Dainippon Pharmaceutical Co., Ltd., Department of Laboratory Products. CPAE cells were subcultured in 10% FCS-Eagle MEM medium charged in a culture flask of 25 cm$^2$. From the cell suspension fractioned upon subculture, 0.1 ml was transferred into a test tube with a sterilized pipette. Then, the cell suspension was diluted to 10 fold with 0.9 ml of Trypan Blue solution and a cell count was counted with a cell counter. After diluting with 10% FCS-Eagle MEM medium so as to have a cell count of $2 \times 10^5$ cells/ml, 100 $\mu$l each/wall, namely, $2 \times 10^4$ cells/wall, of the dilution was dispensed in a 96 wall miorotiter plate (manufactured by Corning) with a micropipette. The plate was incubated at 37° C. in 5% $CO_2$.

The compound of the present invention was dissolved in medium in 0.2 mg/ml; the compound that was insoluble in the medium was dissolved in less than 1% of DMSO and the resulting solution was aseptically filtered through a filter; 5 $\mu$l of the solution was added to the wall with a sterilized micropipette 24 hours after onset of the incubation. After culturing at 37° C. for 72 hours in 5% $CO_2$, the collected culture supernatant was provided for measurement.

The measurement was performed as follows. Plasminogen, 5 μl, was charged in a wall or fibbrin plate (manufactured by Kitazato Institute), which was allowed to stand until diffusion was completed. After diffusion, 5 μl of the supernatant was charged and then put in a carbon dioxide gas incubator of 37° C. Four hours after, evaluation was made by formation of a transparent lysis circle by fibrinolysis. In this case, it was confirmed that a transparent circule was simultaneously formed by fibrinolysis in a wall charged with t-PA as a positive control. A diameter of the transparent circle was 9 to 10 mm.

Also in the case of the supernatant added with the compound of the present invention, a transparent circle due to fibrinolysis showing a diameter of 4.5 to 8.5 mm was noted. However, in the case of the supernatant added with no compound of the present invention (control), no change was noted. In the case of forming a circle of 4 mm or more due to fibrinolysis, it was judged that thrombolytic ability of CPAE cells was induced.

After the fibrinolytic activity was checked over, the wall was fixed with 2.5% of glutaraldehyde in a final concentration. Then, the solution was discarded and the system was washed with PBS. After washing, moisture was removed. After staining with 100 μl of 0.1% crystal violet and allowing stand for 2 to 3 minutes, the system was washed with running water. After an excess of the staining solution was washed out, moisture was removed and the dye bound to the cells was eluted by 100 μl of methanol. Using multiscanning (Titertech), measurements were performed at a wavelength of 580 nm in accordance with the ABS method and the matrix method to confirm that the cells were not injured.

A diameter (mm) of the circle due to fibrinolysis is shown in Table 4. It is clearly seen that the compounds of the present invention showed the thrombolytic activity.

TABLE 4

| Compound No. | Diameter (mm) | Compound No. | Diameter (mm) |
|---|---|---|---|
| 2 | 7.9 | 25 | 4.1 |
| 8 | 6.3 | 26 | 5.7 |
| 9 | 8.2 | 27 | 8.5 |
| 10 | 4.5 | 28 | 8.3 |
| 12 | 5.9 | 29 | 7.1 |
| 14 | 5.9 | 30 | 7.6 |
| 15 | 6.3 | 31 | 7.9 |
| 17 | 7.5 | 32 | 7.5 |
| 18 | 6.8 | 33 | 7.8 |
| 19 | 5.8 | 34 | 7.6 |
| 20 | 8.0 | 35 | 7.8 |
| 21 | 5.6 | 36 | 7.6 |
| 22 | 6.5 | 37 | 6.9 |
| 23 | 8.4 | 38 | 6.9 |
| 24 | 7.6 | 2a | 7.5 |

Thrombolytic activity in vitro

The compounds of the present invention have been shown to be capable of inducing fibrinolytic activity in CPAE cells. In order to verify by what substance in addition to the $a_2$-PI lowering activity, this fibrinolytic activity is induced, analysis was made on the culture solution added with Compound No. 2 out of the compounds of the present invention, by means of fibrin autography.

By SDS-polyacrylamide gel using 10% gel, this culture solution and t-PA (tissue plasminogen activator) and urokinase were subjected to electrophoresis. After the electrophoresis, the gel was treated with 2.5% Triton x-100, which was inoculated on agar plate added with fibrinogen, thrombin and plasminogen. A place of fibrin which caused lysis was confirmed in an incubator of 37° C. in 5% $CO_2$.

As a result, great fibrinolysis was noted in the culture supernatant added with the compound of the present invention, at the position of molecular weight of urokinase type plasminogen activator. It was made clear that the compound of the present invention strongly induced production of urokinase type plasminogen activator in CPAE.

Test on acute toxicity:

Four (4) ddY strain male mice of 6 week age were used for each group of the test sample.

Method:

In intravenous administration, each sample was dissolved in 0.9% physiological saline and the solution was administered through the tail vein. In intraperiotoneal administration, each sample was suspended in 0.5% CMC-physiological saline and 0.1 ml of the suspension per 10 mg of mouse body weight was intraperitoneally administered. In oral administration, each sample was suspended in 0.5% CMC-physiological saline and 0.2 ml of the suspension per 10 mg of mouse body weight was orally administered.

Observation was made immediately after the administration. After observation for 1 week after the administration, the mice was sacrificed with chloroform and subjected to autopsy.

$LD_{50}$ of each sample is summarized in the following table. Safety of the compounds of the present invention are clearly shown.

| (Compound No.) | $LD_{50}$ (mg/kg) |
|---|---|
| Intravenous administration: | |
| 1 | 3235 |
| 2 | 5091 |
| Intraperitoneal administration: | |
| 1 | 5,000 |
| 2 | 10,000 |
| Oral administration: | |
| 1 | 7,500 |
| 2 | 10,000 |

The following examples illustrate the formulation of pharmaceutical compositions according to the present invention:

EXAMPLE 1

Per 1 tablet, the following compounds were added to the compound (Compound No. 2) of the present invention and tablets were obtained in a conventional manner.

| Per tablet (in 300 mg) | |
|---|---|
| Compound of the present invention (Compound No. 2) | 200 mg |
| Lactose | 50 mg |
| Corn starch | 20 mg |
| Low substitution degree hydroxypropyl cellulose | 15 mg |
| Hydroxypropyl cellulose | 5 mg |
| Magnesium stearate | 10 mg |
| | 300 mg |

EXAMPLE 2

Per 1 ampoule, the following compounds were ddded to the compound (Compound No. 2) of the present invention and ampoules for injection were obtained in a conventional manner.

| Per ampoule (in 10 ml) | |
|---|---|
| Compound of the present invention (Compound No. 2) | 200 mg |
| Sodium chloride | 90 mg |
| Distilled water for injection | c.s. |
| | 10 ml |

What is claimed is:

1. A method of lowering the activity of an $\alpha_2$-plasmin inhibitor which comprises administering to a human or an animal in need thereof an effective amount sufficient to lower the activity of an $\alpha_2$-plasmin inhibitor of a compound selected from the group consisting of:

a. A compound of the formula

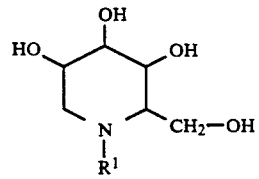

,a pharmaceutically acceptable acid addition salt thereof or a quaternary salt thereof wherein $R^1$ is hydrogen, alkyl of 1 to 10 carbon atoms, carboxyalkyl of 1 to 10 carbon atoms in the alkyl moiety, lower alkyloxycarbonylalkyl of 1 to 10 carbon atoms in the alkyl moiety, hydroxyalkyl of 1 to 10 carbon atoms in the alkyl moiety, cycloalkyl lower alkyl wherein the cycloalkyl moiety is of 3 to 7 carbon atoms, aryl lower alkyl, aryloxy lower alkyl, alkenyl of 2 to 10 carbon atoms or arylalkenyl of 2 to 10 carbon atoms in the alkenyl moiety.

2. A method according to claim 1 wherein $R^1$ is hydrogen, lower alkyl, carboxy lower alkyl, lower alkyloxy carbonyl lower alkyl, hydroxy lower alkyl, cycloalkyl lower alkyl of 3 to 5 carbon atoms in the cycloalkyl moiety, aryl lower alkyl, aryloxy lower alkyl, lower alkenyl or aryl lower alkenyl wherein the aryl moiety is phenyl or naphthyl.

* * * * *